(12) United States Patent
Narula et al.

(10) Patent No.: US 8,183,200 B1
(45) Date of Patent: May 22, 2012

(54) ORGANOLEPTIC COMPOUNDS

(75) Inventors: Anubhav P. S. Narula, Hazlet, NJ (US);
Richard M. Boden, Ocean, NJ (US);
James A. Lasome, Matawan, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/970,129

(22) Filed: Dec. 16, 2010

(51) Int. Cl.
*C11B 9/00* (2006.01)
*A61K 8/33* (2006.01)
*A61K 8/49* (2006.01)

(52) U.S. Cl. ............ 512/13; 512/8; 512/11; 512/14; 510/104; 549/360; 549/386

(58) Field of Classification Search ......... 512/8, 11, 512/13, 14; 510/103, 104; 549/360, 386
See application file for complete search history.

(56) References Cited

U.S. PATENT DOCUMENTS

| | | | | |
|---|---|---|---|---|
| 5,081,262 A | * | 1/1992 | Narula et al. | 549/355 |
| 5,128,317 A | * | 7/1992 | Narula et al. | 512/13 |
| 5,240,907 A | * | 8/1993 | Narula et al. | 512/8 |
| 2011/0182832 A1 | * | 7/2011 | Bradshaw et al. | 424/49 |

OTHER PUBLICATIONS

Locicero, J.C., et al., "The OXO Reaction of Camphene. Structure of the Aldehyde and Derivatives." J. Am. Chem. Soc. 1952, 74(8), pp. 2094-2097.

* cited by examiner

*Primary Examiner* — James J Seidleck
*Assistant Examiner* — Saira B Haider
(74) *Attorney, Agent, or Firm* — Elizabeth M. Quirk; XuFan Tseng; Joseph F. Leightner

(57) ABSTRACT

The present invention is directed to novel fragrance compounds and their unexpected advantageous use in improving, enhancing or modifying a fragrance formulation through the addition of an olfactory acceptable amount of the compounds, wherein the compounds are represented by the following formula:

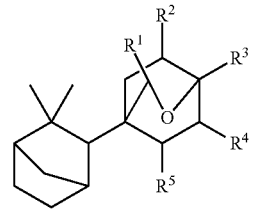

wherein $R^1$, $R^2$, $R^3$, $R^4$, and $R^5$ are independently selected from the group consisting of hydrogen and $C_1$-$C_5$ alkyl.

20 Claims, No Drawings

ORGANOLEPTIC COMPOUNDS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides novel chemicals and their unexpected advantageous use in improving, enhancing or modifying the fragrance of perfumes, colognes, toilet waters, personal products, fabric care products, and the like.

One embodiment of the present invention is directed to novel substituted novel 2-oxa-bicyclo[2.2.2]octane derivative compounds represented by the following formula:

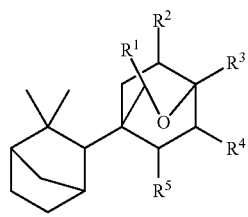

Structure I wherein $R^1$, $R^2$, $R^3$, $R^4$, and $R^5$ are independently selected from the group consisting of hydrogen and $C_1$-$C_5$ alkyl.

Another embodiment of the present invention is directed to the use of the compounds provided above as fragrance materials in perfumes, colognes, toilet waters, personal products, fabric care products, and the like.

Another embodiment of the present invention is directed to a fragrance composition comprising the compounds provided above.

Another embodiment of the present invention is directed to a fragrance product comprising the compounds provided above.

Another embodiment of the present invention is directed to a method of improving, enhancing or modifying a fragrance formulation by incorporating an olfactory acceptable amount of the compounds provided above.

These and other embodiments of the present invention will be apparent by reading the following specification.

DETAILED DESCRIPTION OF THE INVENTION

It has been surprisingly found that the compounds of the present invention provide unexpected strong woody character.

In one embodiment of the present invention, the compounds of the present invention are represented by the following structures:

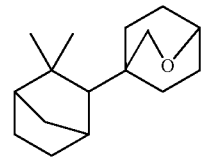

Structure II

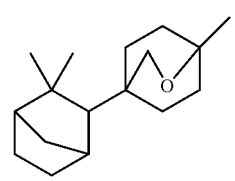

Structure III

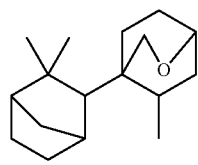

Structure IV

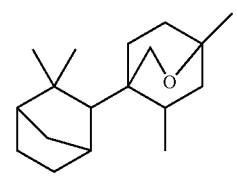

Structure V

Those with skill in the art will recognize that:

Structure II is 4-(3,3-dimethyl-bicyclo[2.2.1]hept-2-yl)-2-oxa-bicyclo[2.2.2]octane;

Structure III is 4-(3,3-dimethyl-bicyclo[2.2.1]hept-2-yl)-1-methyl-2-oxa-bicyclo[2.2.2]octane;

Structure IV is 4-(3,3-dimethyl-bicyclo[2.2.1]hept-2-yl)-5-methyl-2-oxa-bicyclo[2.2.2]octane; and Structure V is 4-(3,3-dimethyl-bicyclo[2.2.1]hept-2-yl)-1,5-dimethyl-2-oxa-bicyclo[2.2.2]octane.

The compounds of the present invention were prepared with aldehydes according to the following reaction scheme, the details of which are specified in the Examples. Materials and catalysts were purchased from Aldrich Chemical Company unless noted otherwise.

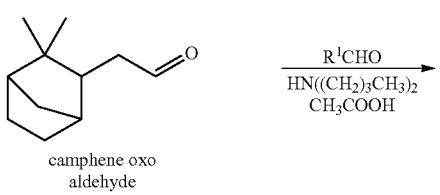

camphene oxo aldehyde

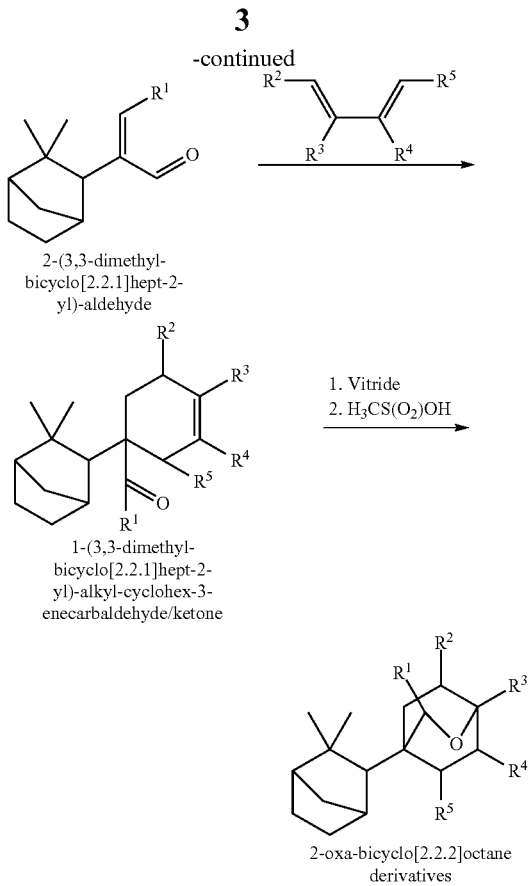

2-(3,3-dimethyl-bicyclo[2.2.1]hept-2-yl)-aldehyde

1. Vitride
2. H₃CS(O₂)OH 1-(3,3-dimethyl-bicyclo[2.2.1]hept-2-yl)-alkyl-cyclohex-3-enecarbaldehyde/ketone 2-oxa-bicyclo[2.2.2]octane derivatives wherein R¹, R², R³, R⁴, and R⁵ are defined as above.

Those with skill in the art will recognize that some of the compounds of the present invention have a number of chiral centers, thereby providing numerous isomers of the claimed compounds. Those with skill in the art will further recognize that the above reaction scheme contains a thermal Diels-Alder reaction that leads to the formation of regio-structural isomers such as para- and meta-isomers. It is intended herein that the compounds described herein include isomeric mixtures of such compounds. The isomers can be separated using techniques known to those with skill in the art. Suitable techniques include chromatography such as high performance liquid chromatography, referred to as HPLC, particularly silica gel chromatograph, and gas chromatography trapping known as GC trapping. Otherwise, those with skill in the art will appreciate a Lewis acid catalyzed Diels-Alder reaction that leads to a product containing predominant amount of para-isomers. Yet, commercial versions of Diels-Alder products are mostly offered as mixtures.

The compounds of the present invention, for example, possess the following fragrance notes:

4-(3,3-dimethyl-bicyclo[2.2.1]hept-2-yl)-2-oxa-bicyclo [2.2.2]octane (Structure II) possesses woody, cedar-like, creamy, and earthy notes;

4-(3,3-dimethyl-bicyclo[2.2.1]hept-2-yl)-1-methyl-2-oxa-bicyclo[2.2.2]octane (Structure III) possesses woody, animalic, phenolic in water, leather, amber, sweet, and slightly fruity notes;

4-(3,3-dimethyl-bicyclo[2.2.1]hept-2-yl)-5-methyl-2-oxa-bicyclo[2.2.2]octane (Structure IV) possesses woody, fresh, dry, and amber notes; and 4-(3,3-dimethyl-bicyclo[2.2.1]hept-2-yl)-1,5-dimethyl-2-oxa-bicyclo[2.2.2]octane (Structure V) possesses woody and onion notes.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The terms "fragrance formulation", "fragrance composition", and "perfume composition" are understood to mean the same and refer to a formulation that is intended for providing a fragrance character to a perfume, a cologne, toilet water, a personal product, a fabric care product, and the like. The fragrance formulation of the present invention is a composition comprising a compound of the present invention.

Olfactory acceptable amount is understood to mean the amount of a compound in a perfume composition. The compound will contribute its particular olfactory characteristics, but the olfactory effect of the perfume composition will be the sum of the effects of each of the perfumes or fragrance ingredients. Thus the compounds of the invention can be used to alter the aroma characteristics of a perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, mol is understood to be mole, L is understood to be liter, mL is understood to be milliliter, Kg is understood to be kilogram and g be gram, psi is understood to be pound-force per square inch, and mmHg is understood to be millimeters (mm) of mercury (Hg). IFF as used in the examples is understood to mean International Flavors & Fragrances Inc., New York, N.Y., USA.

EXAMPLE I

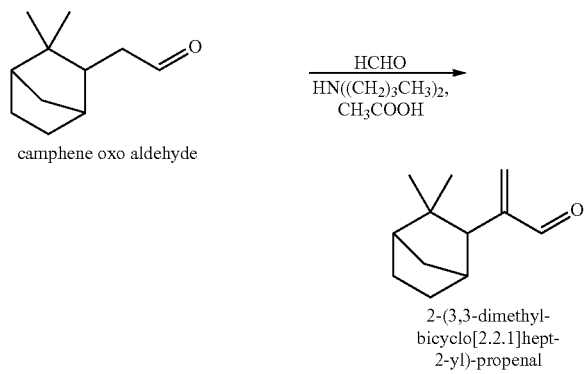

camphene oxo aldehyde 2-(3,3-dimethyl-bicyclo[2.2.1]hept-2-yl)-propenal

Preparation of 2-(3,3-Dimethyl-bicyclo[2.2.1]hept-2-yl)-propenal: A 2-L Morton flask equipped with a stirrer, a thermometer, a reflux condenser, a heating mantle, and an addition funnel was charged with di-n-butylamine ($HN((CH_2)_3CH_3)_2$, 16.8 g, 0.13 mol) and acetic acid ($CH_3COOH$, 15.7 g, 0.26 mol). The temperature of the resulting reaction mass rose to 50° C., which was rapidly cooled to 38° C. Formaldehyde (HCHO, 37%, 214 g, 2.6 mol) was added and the reaction mass was heated to 78° C. Camphene oxo aldehyde (418.5 g, 2.2 mol) was synthesized as previously described [LoCicero, et al., J. Am. Chem. Soc. 1952, 74(8): 2094-2097] and fed into the reaction mass over about 1.5 hours. The reaction mass was stirred for additional 4 hours while the temperature was maintained at 78-80° C. The organic layer was sequentially washed with water (1 L), saturated sodium chloride (NaCl, 1 L), sodium bicarbonate ($NaHCO_3$, 10%, 1 L), and saturated sodium chloride (1 L), and filtered through anhydrous magnesium sulfate ($MgSO_4$) to provide a crude product (431 g). Gas chromatography test indicated in the crude produce a mixture containing 2-(3,3-dimethyl-bicyclo[2.2.1]hept-2-yl)-propenal (76%) and camphene oxo aldehyde (2.8%). Further fractional distillation provided 2-(3,3-dimethyl-bicyclo [2.2.1]hept-2-yl)-propenal (328 g).

$^1$H NMR ($CDCl_3$, 500 MHz): 0.6 ppm (s, 3H); 0.7 ppm (s, 3H); 1.15-1.36 ppm (m, 6H); 1.55-1.85 ppm (m, 6H); 2.15-2.53 ppm (m, 3H); 6.0 ppm (d, 1H); 6.35 ppm (d, 1H); 9.5 ppm (d, 1H).

EXAMPLE II

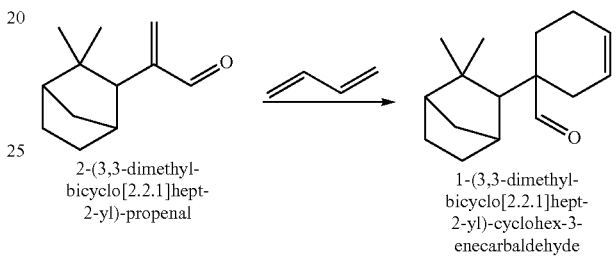

2-(3,3-dimethyl-bicyclo[2.2.1]hept-2-yl)-propenal 1-(3,3-dimethyl-bicyclo[2.2.1]hept-2-yl)-cyclohex-3-enecarbaldehyde Preparation of 1-(3,3-Dimethyl-bicyclo[2.2.1]hept-2-yl)-cyclohex-3-enecarbaldehyde: A 2-L Parr Bomb was charged with 2-(3,3-dimethyl-bicyclo[2.2.1]hept-2-yl)-propenal (750 g, 3.83 mol, synthesized as above in EXAMPLE I) and butadiene ($CH_2$=CH—CH=$CH_2$, 310.5 g, 5.75 mol). The Parr Bomb was closed and purged with nitrogen gas to 60 psi. The temperature was raised to 180° C. and the pressure was raised to 340 psig. The Parr Bomb was maintained at 180° C. for 6 hours before cooled. The Parr Bomb was opened and the resulting reaction mass was fractionally distilled to provide the Diels-Alder product (1099 g) containing 1-(3,3-dimethyl-bicyclo[2.2.1]hept-2-yl)-cyclohex-3-enecarbaldehyde having a boiling point of 142° C. at a pressure of 3 mmHg.

$^1$H NMR ($CDCl_3$, 500 MHz): 0.98-1.08 ppm (m, 6H); 1.10-2.70 ppm (m, 15H); 5.57-5.72 ppm (m, 2H); 9.58-9.84 ppm (m, 1H).

The above product possessed woody, weak, and slightly animalic notes.

EXAMPLE III

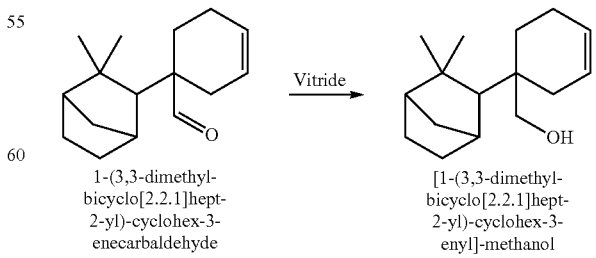

1-(3,3-dimethyl-bicyclo[2.2.1]hept-2-yl)-cyclohex-3-enecarbaldehyde

[1-(3,3-dimethyl-bicyclo[2.2.1]hept-2-yl)-cyclohex-3-enyl]-methanol

Preparation of [1-(3,3-Dimethyl-bicyclo[2.2.1]hept-2-yl)-cyclohex-3-enyl]-methanol: A 1-L reaction flask equipped with a stirrer, a thermometer, a reflux condenser, a heating mantle, and an addition funnel was charged with Vitride (226 g, 0.73 mol) and toluene (226 g). The resulting mixture was stirred at 20° C. The Diels-Alder product containing 1-(3,3-dimethyl-bicyclo[2.2.1]hept-2-yl)-cyclohex-3-enecarbaldehyde (310 g, 1.32 mol, synthesized as above in EXAMPLE II) was added over about 2 hours. The temperature was allowed to rise to 45° C. The reaction mass was aged for 2.5 hours. The excessive Vitride reagent was quenched with ethyl acetate ($CH_3CO_2CH_2CH_3$, 44 g), followed by sodium hydroxide (NaOH, 25%, 467 g). The temperature was allowed to rise to 50° C. and stirred for another 0.5 hours. The organic phase was diluted with toluene (100 mL), washed with hot water (1 L) twice, and then concentrated to yield the crude product [1-(3,3-dimethyl-bicyclo[2.2.1]hept-2-yl)-cyclohex-3-enyl]-methanol (390 g) having a boiling point of 153° C. at a pressure of 1.7 mmHg.

$^1$H NMR ($CDCl_3$, 500 MHz): 1.02-1.20 ppm (m, 8H); 1.22-1.39 ppm (m, 2H); 1.45-1.81 ppm (m, 7H); 1.83-2.53 ppm (m, 5H); 3.43-3.71 ppm (m, 2H); 5.52-5.61 ppm (m, 1H); 5.62-5.69 ppm (m, 1H).

EXAMPLE IV

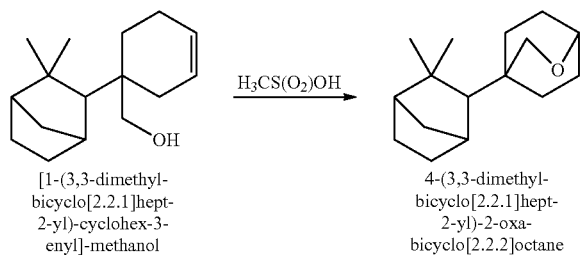

[1-(3,3-dimethyl-bicyclo[2.2.1]hept-2-yl)-cyclohex-3-enyl]-methanol 4-(3,3-dimethyl-bicyclo[2.2.1]hept-2-yl)-2-oxa-bicyclo[2.2.2]octane Preparation of 4-(3,3-Dimethyl-bicyclo[2.2.1]hept-2-yl)-2-oxa-bicyclo[2.2.2]octane (Structure II): A 1-L reaction flask equipped with a stirrer, a thermometer, a reflux condenser, a heating mantle, and an addition funnel was charged with the crude product [1-(3,3-dimethyl-bicyclo[2.2.1]hept-2-yl)-cyclohex-3-enyl]-methanol (267 g, 1.15 mol, synthesized as above in EXAMPLE III) and toluene (300 mL). The temperature was maintained at 25° C. Methane sulfonic acid ($H_3CS(O_2)OH$, 20 g, 207 mmol) was slowly added to the reaction mass over about 5 minutes. The reaction mass was stirred, heated to 85° C., aged for 16 hours, and then cooled to 50° C. Sodium hydroxide (20 g, 200 mL) and toluene (500 mL) were added. The reaction mass was stirred for another 0.5 hours. The organic phase was separated, washed with saturated sodium chloride (250 mL), and filtered through anhydrous magnesium sulfate. Fractional distillation provided an isomer mixture (187 g) containing the major product 4-(3,3-dimethyl-bicyclo[2.2.1]hept-2-yl)-2-oxa-bicyclo[2.2.2]octane having a boiling point of 136° C. at a pressure of 1.3 mmHg.

$^1$H NMR ($CDCl_3$, 500 MHz): 0.94-1.15 ppm (m, 6H); 1.20-1.38 ppm (m, 3H); 1.39-1.80 ppm (m, 12H); 1.89-2.01 ppm (m, 1H); 2.02-2.32 ppm (m, 1H); 3.49-3.84 ppm (m, 1H); 3.85-3.97 ppm (m, 1H); 4.20-4.28 ppm (m, 1H).

The above product possessed woody, cedar-like, creamy, and earthy notes.

EXAMPLE V

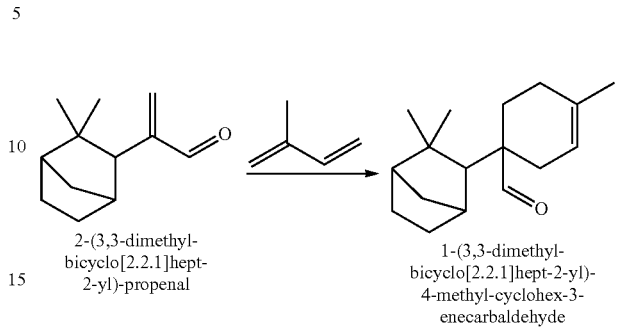

2-(3,3-dimethyl-bicyclo[2.2.1]hept-2-yl)-propenal 1-(3,3-dimethyl-bicyclo[2.2.1]hept-2-yl)-4-methyl-cyclohex-3-enecarbaldehyde Preparation of 1-(3,3-Dimethyl-bicyclo[2.2.1]hept-2-yl)-4-methyl-cyclohex-3-enecarbaldehyde: A 1-L Parr Bomb was charged with 2-(3,3-dimethyl-bicyclo[2.2.1]hept-2-yl)-propenal (193 g, 1 mol, synthesized as above in EXAMPLE I) and isoprene ($CH_2=C(CH_3)CH=CH_2$, 89 g, 1.3 mol). The Parr Bomb was closed and purged with nitrogen gas to 60 psi. The temperature was raised to 150° C. and the pressure to 180 psig. The Parr Bomb was maintained at 150° C. for 12 hours before cooled. The Parr Bomb was opened and the resulting reaction mass was fractionally distilled to provide the Diels-Alder product (339 g) containing the major product 1-(3,3-dimethyl-bicyclo[2.2.1]hept-2-yl)-4-methyl-cyclohex-3-enecarbaldehyde having a boiling point at 115-124° C. at a pressure of 1.5 mmHg.

$^1$H NMR ($CDCl_3$, 500 MHz): 0.97-1.10 ppm (m, 6H); 1.11-1.20 ppm (m, 2H); 1.23-1.49 ppm (m, 3H); 1.58-1.79 ppm (m, 7H); 1.80-2.14 ppm (m, 4H); 2.24-2.66 ppm (m, 2H); 5.28-5.39 ppm (m, 1H); 9.50-9.82 ppm (m, 1H).

EXAMPLE VI

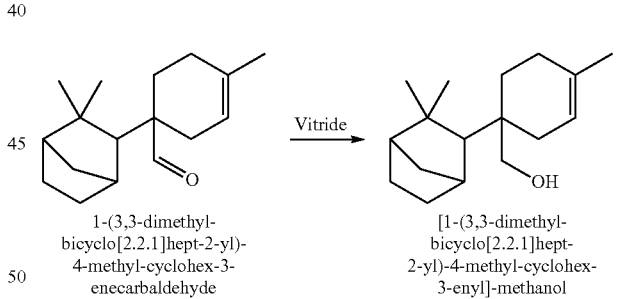

1-(3,3-dimethyl-bicyclo[2.2.1]hept-2-yl)-4-methyl-cyclohex-3-enecarbaldehyde

[1-(3,3-dimethyl-bicyclo[2.2.1]hept-2-yl)-4-methyl-cyclohex-3-enyl]-methanol

Preparation of [1-(3,3-Dimethyl-bicyclo[2.2.1]hept-2-yl)-4-methyl-cyclohex-3-enyl]-methanol: A 1-L reaction flask equipped with a stirrer, a thermometer, a reflux condenser, a heating mantle, and an addition funnel was charged with Vitride (260 g, 0.84 mol) and toluene (260 g). The resulting mixture was stirred at 20° C. The Diels-Alder product containing 1-(3,3-dimethyl-bicyclo[2.2.1]hept-2-yl)-4-methyl-cyclohex-3-enecarbaldehyde (275 g, 1.16 mol, synthesized as above in EXAMPLE V) was added over about 2 hours. The temperature was allowed to rise to 40° C. The reaction mass was aged for 3 hours. The excessive Vitride reagent was quenched with ethyl acetate (22 g), followed by sodium hydroxide (25%, 134 g). The temperature was allowed to rise to 50° C. and stirred for another 0.5 hours. The organic phase was washed with hot water (1 L) twice and concentrated to yield the crude product [1-(3,3-dimethyl-bicyclo[2.2.1]hept-2-yl)-4-methyl-cyclohex-3-enyl]-methanol (250 g, 0.96 mol).

EXAMPLE VII

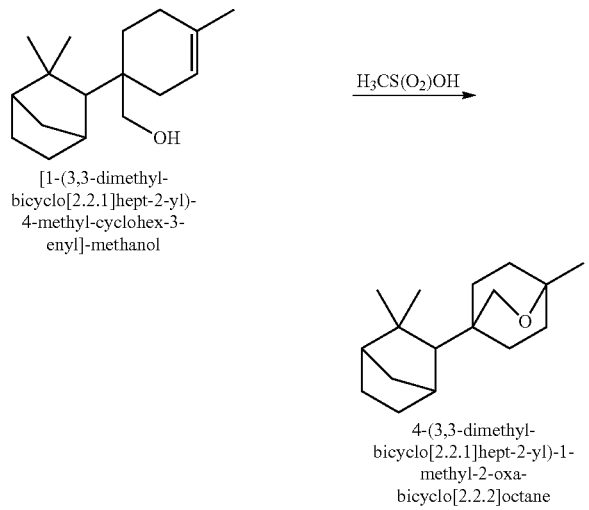

[1-(3,3-dimethyl-bicyclo[2.2.1]hept-2-yl)-4-methyl-cyclohex-3-enyl]-methanol $\xrightarrow{H_3CS(O_2)OH}$ 4-(3,3-dimethyl-bicyclo[2.2.1]hept-2-yl)-1-methyl-2-oxa-bicyclo[2.2.2]octane Preparation of 4-(3,3-Dimethyl-bicyclo[2.2.1]hept-2-yl)-1-methyl-2-oxa-bicyclo[2.2.2]octane (Structure III): A 1-L reaction flask equipped with a stirrer, a thermometer, a reflux condenser, a heating mantle, and an addition funnel was charged with the crude product [1-(3,3-dimethyl-bicyclo[2.2.1]hept-2-yl)-4-methyl-cyclohex-3-enyl]-methanol (258 g, 0.96 mol, synthesized as above in EXAMPLE VI) and nitropropane (250 mL). The temperature was maintained at 25° C. Methane sulfonic acid (8.4 g, 87 mmol) was slowly added to the reaction mass over about 5 minutes. The reaction mass was stirred, heated to 70° C., aged for 6.5 hours, and then cooled to 50° C. Sodium methoxide (CH$_3$ONa, 10 g) and toluene (500 mL) were added. The reaction mass was stirred for another 0.5 hours. Water (100 mL) was then added and the organic phase was separated, washed with saturated sodium chloride (250 mL), and filtered through anhydrous magnesium sulfate. Fractional distillation provided an isomer mixture (162 g) containing the major product 4-(3,3-dimethyl-bicyclo[2.2.1]hept-2-yl)-1-methyl-2-oxa-bicyclo[2.2.2]octane having a boiling point of 127° C. at a pressure of 1.4 mmHg.

$^1$H NMR (CDCl$_3$, 500 MHz): 0.76-0.91 ppm (m, 6H); 0.95-1.16 ppm (m, 7H); 1.23-1.46 ppm (m, 5H); 1.47-1.61 ppm (m, 4H); 1.65-1.81 ppm (m, 4H); 3.60-4.04 ppm (m, 2H).

The above product possessed woody, animalic, phenolic in water, leather, amber, sweet, and slightly fruity notes.

EXAMPLE VIII

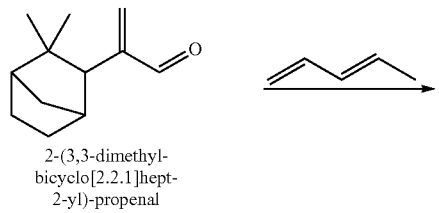

2-(3,3-dimethyl-bicyclo[2.2.1]hept-2-yl)-propenal

-continued

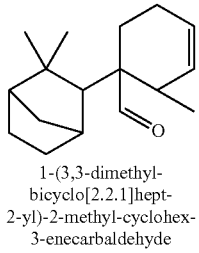

1-(3,3-dimethyl-bicyclo[2.2.1]hept-2-yl)-2-methyl-cyclohex-3-enecarbaldehyde

Preparation of 1-(3,3-Dimethyl-bicyclo[2.2.1]hept-2-yl)-2-methyl-cyclohex-3-enecarbaldehyde: A 2-L Parr Bomb was charged with 2-(3,3-dimethyl-bicyclo[2.2.1]hept-2-yl)-propenal (574.5 g, 3 mol, synthesized as above in EXAMPLE I) and piperylene (CH$_2$=CHCH=CHCH$_3$, 265.5 g, 3.9 mol). The Parr Bomb was closed and purged with nitrogen gas to 60 psi. The temperature was raised to 150° C. and the pressure to 200 psig. The Parr Bomb was maintained at 150-180° C. for 13 hours before cooled. The Parr Bomb was opened and the resulting reaction mass was fractionally distilled to provide the Diels-Alder product (416.5 g) containing 1-(3,3-dimethyl-bicyclo[2.2.1]hept-2-yl)-2-methyl-cyclohex-3-enecarbaldehyde having a boiling point of 143° C. at a pressure of 0.71 mmHg.

$^1$H NMR (CDCl$_3$, 500 MHz): 0.61-1.28 ppm (m, 10H); 1.31-2.74 ppm (m, 13H); 5.44-6.38 ppm (m, 2H); 9.50-10.25 ppm (m, 1H).

The above product possessed fruity, woody, and dry notes.

EXAMPLE IX

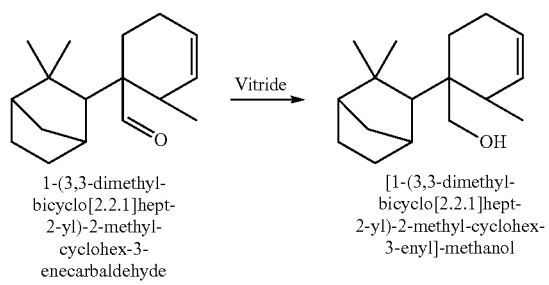

1-(3,3-dimethyl-bicyclo[2.2.1]hept-2-yl)-2-methyl-cyclohex-3-enecarbaldehyde

Vitride →

[1-(3,3-dimethyl-bicyclo[2.2.1]hept-2-yl)-2-methyl-cyclohex-3-enyl]-methanol

Preparation of [1-(3,3-Dimethyl-bicyclo[2.2.1]hept-2-yl)-2-methyl-cyclohex-3-enyl]-methanol: A 1-L reaction flask equipped with a stirrer, a thermometer, a reflux condenser, a heating mantle, and an addition funnel was charged with Vitride (300 g, 1.32 mol) and toluene (300 g). The resulting mixture was stirred at 20° C. The Diels-Alder product containing 1-(3,3-dimethyl-bicyclo[2.2.1]hept-2-yl)-2-methyl-cyclohex-3-enecarbaldehyde (300 g, 0.97 mol, synthesized as above in EXAMPLE VIII) was added over about 2 hours. The temperature was allowed to rise to 43° C. The reaction mass was aged for 3 hours. The excessive Vitride reagent was quenched with ethyl acetate (100 g), followed by sodium hydroxide (25%, 800 g). The temperature was allowed to rise to 50° C. and stirred for another 0.5 hours. The organic phase was washed with hot water (1 L) twice and concentrated to yield the crude product [1-(3,3-dimethyl-bicyclo[2.2.1]hept-2-yl)-2-methyl-cyclohex-3-enyl]-methanol (295 g).

EXAMPLE X

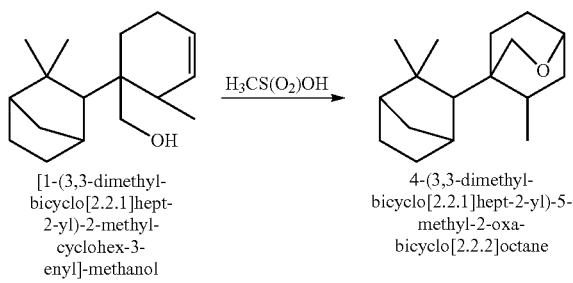

[1-(3,3-dimethyl-bicyclo[2.2.1]hept-2-yl)-2-methyl-cyclohex-3-enyl]-methanol 4-(3,3-dimethyl-bicyclo[2.2.1]hept-2-yl)-5-methyl-2-oxa-bicyclo[2.2.2]octane Preparation of 4-(3,3-Dimethyl-bicyclo[2.2.1]hept-2-yl)-5-methyl-2-oxa-bicyclo[2.2.2]octane (Structure IV): A 1-L reaction flask equipped with a stirrer, a thermometer, a reflux condenser, a heating mantle, and an addition funnel was charged with the crude product [1-(3,3-dimethyl-bicyclo[2.2.1]hept-2-yl)-2-methyl-cyclohex-3-enyl]-methanol (290 g, 1.16 mol, synthesized as above in EXAMPLE IX) and toluene (800 mL). The temperature was maintained at 25° C. Methane sulfonic acid (5.8 g, 60 mmol) was slowly added to the reaction mass over about 5 minutes. The reaction mass was stirred, heated to 85° C., aged for 7.8 hours, and then cooled to 50° C. Sodium methoxide (10 g) and toluene (500 mL) were added. The reaction mass was stirred for another 0.5 hours. Water (100 mL) was then added and the organic phase was separated, washed with sodium hydroxide followed by saturated sodium chloride (250 mL), and filtered through anhydrous magnesium sulfate. Fractional distillation provided an isomer mixture (250 g) containing the major product 4-(3,3-dimethyl-bicyclo[2.2.1]hept-2-yl)-5-methyl-2-oxa-bicyclo [2.2.2]octane.

$^1$H NMR (CDCl$_3$, 500 MHz): 0.89-2.24 ppm (m, 25H); 3.52-3.74 ppm (m, 1H); 3.82-4.03 ppm (m, 2H).

The above product possessed woody, fresh, dry, and amber notes.

EXAMPLE XI

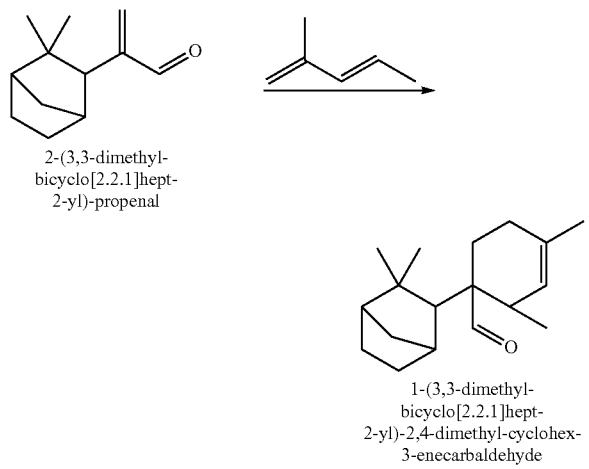

2-(3,3-dimethyl-bicyclo[2.2.1]hept-2-yl)-propenal 1-(3,3-dimethyl-bicyclo[2.2.1]hept-2-yl)-2,4-dimethyl-cyclohex-3-enecarbaldehyde Preparation of 1-(3,3-Dimethyl-bicyclo[2.2.1]hept-2-yl)-2,4-dimethyl-cyclohex-3-enecarbaldehyde: A 2-L Parr Bomb was charged with 2-(3,3-dimethyl-bicyclo[2.2.1]hept-2-yl)-propenal (750 g, 3.79 mol, synthesized as above in EXAMPLE I) and methyl pentadiene (CH$_2$=C(CH$_3$)CH=CHCH$_3$, 418.5 g, 5.1 mol). The Parr Bomb was closed and purged with nitrogen gas to 60 psi. The temperature was raised to 180° C. and the pressure to 125 psig. The Parr Bomb was maintained at 180° C. for 6 hours before cooled. The Parr Bomb was opened and the resulting reaction mass was fractionally distilled to provide the Diels-Alder product (339 g) containing the major product 1-(3,3-dimethyl-bicyclo[2.2.1]hept-2-yl)-2,4-dimethyl-cyclohex-3-enecarbaldehyde having a boiling point of 148° C. at a pressure of 1 mmHg.

$^1$H NMR (CDCl$_3$, 500 MHz): 0.76-2.72 ppm (m, 26H); 5.17-5.61 ppm (m, 1H); 9.61-10.23 ppm (m, 1H).

The above product possessed woody and smoky notes.

EXAMPLE XII

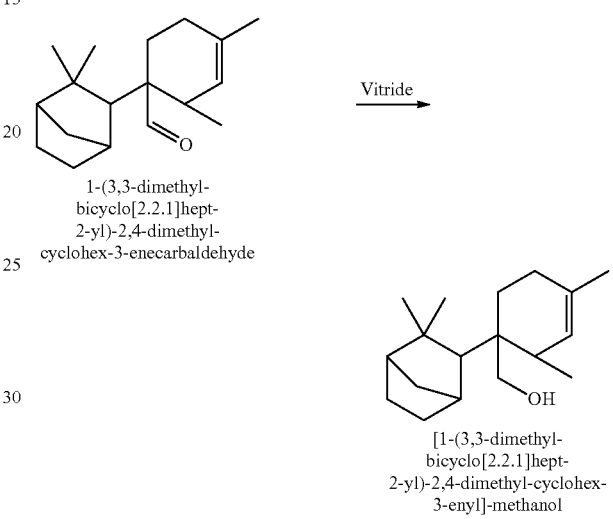

1-(3,3-dimethyl-bicyclo[2.2.1]hept-2-yl)-2,4-dimethyl-cyclohex-3-enecarbaldehyde

[1-(3,3-dimethyl-bicyclo[2.2.1]hept-2-yl)-2,4-dimethyl-cyclohex-3-enyl]-methanol Preparation of [1-(3,3-Dimethyl-bicyclo[2.2.1]hept-2-yl)-2,4-dimethyl-cyclohex-3-enyl]-methanol: A 3-L reaction flask equipped with a stirrer, a thermometer, a reflux condenser, a heating mantle, and an addition funnel was charged with Vitride (1112 g, 3.5 mol) and toluene (1 Kg). The resulting mixture was stirred at 21.2° C. The Diels-Alder product containing 1-(3,3-dimethyl-bicyclo[2.2.1]hept-2-yl)-2,4-dimethyl-cyclohex-3-enecarbaldehyde (778.5 g, 2.59 mol, synthesized as above in EXAMPLE XI) was added over about 4 hours. The temperature was allowed to rise to 35° C. The reaction mass was aged for 1 hour. The excessive Vitride reagent was quenched with ethyl acetate (125 g), followed by sodium hydroxide (30%, 3 Kg). The temperature was allowed to rise to 40° C. and stirred for another 0.5 hours. The organic phase was washed with hot water (1 L) twice and distilled to yield the crude product [1-(3,3-dimethyl-bicyclo[2.2.1]hept-2-yl)-2,4-dimethyl-cyclohex-3-enyl]-methanol (829.5 g).

EXAMPLE XIII

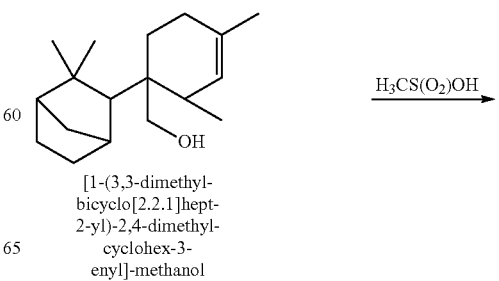

[1-(3,3-dimethyl-bicyclo[2.2.1]hept-2-yl)-2,4-dimethyl-cyclohex-3-enyl]-methanol

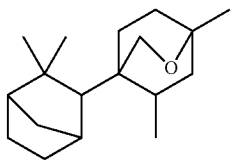

4-(3,3-dimethyl-
bicyclo[2.2.1]hept-
2-yl)-1,5-dimethyl-2-oxa-
bicyclo[2.2.2]octane Preparation of 4-(3,3-Dimethyl-bicyclo[2.2.1]hept-2-yl)-1,5-dimethyl-2-oxa-bicyclo[2.2.2]octane (Structure V): A 2-L reaction flask equipped with a stirrer, a thermometer, a reflux condenser, a heating mantle, and an addition funnel was charged with the crude product [1-(3,3-dimethyl-bicyclo[2.2.1]hept-2-yl)-2,4-dimethyl-cyclohex-3-enyl]-methanol (612 g, 2.22 mol, synthesized as above in EXAMPLE XII) and toluene (580.5 mL). The temperature was maintained at 25° C. Methane sulfonic acid (10.7 g, 111 mmol) was slowly added to the reaction mass over about 5 minutes. The reaction mass was stirred, heated to 80° C., aged for 6.5 hours, and then cooled to 40° C. Sodium hydroxide (20%, 200 g) and toluene (500 mL) were added. The reaction mass was stirred for another 0.5 hours. The organic phase was separated, washed with sodium hydroxide followed by saturated sodium chloride (250 mL) twice, and filtered through anhydrous magnesium sulfate. Fractional distillation provided an isomer mixture (1189.5 g) containing 4-(3,3-dimethyl-bicyclo[2.2.1]hept-2-yl)-1,5-dimethyl-2-oxa-bicyclo[2.2.2]octane having a boiling point of 146° C. at a pressure of 0.62 mmHg.

$^1$H NMR (CDCl$_3$, 500 MHz): 0.86-1.19 ppm (m, 14H); 1.22-2.29 ppm (m, 14H); 3.50-4.02 ppm (m, 2H).

4-(3,3-Dimethyl-bicyclo[2.2.1]hept-2-yl)-1,5-dimethyl-2-oxa-bicyclo[2.2.2]octane possessed woody and onion notes.

EXAMPLE XIV

Fragrance formulation containing 4-(3,3-dimethyl-bicyclo[2.2.1]hept-2-yl)-1-methyl-2-oxa-bicyclo[2.2.2]octane (Structure III):

| Fragrance Ingredient | Parts by Weight |
|---|---|
| Indisan neat | 20.60 |
| Meth DH Jasmonate BHT | 16.00 |
| Ethylene Brassylate (Astratone) | 13.00 |
| Zenolide | 12.30 |
| Lyral BHT | 6.60 |
| Structure III | 6.60 |
| Floriffol (ELINCS) | 5.60 |
| Linalyl Acet | 5.60 |
| Phenyl Eth Alc White Extra | 2.30 |
| Citronellol Coeur | 1.20 |
| Phenoxanol | 1.00 |
| Nerol Coeur 10% DPG | 1.00 |
| Magnolan | 1.00 |
| Geraniol Coeur | 1.00 |
| Damascone, delta BHT 10% DPG | 0.70 |
| Geranyl acetate pure 10% DPG | 0.50 |
| Eth vanillin | 0.20 |
| Undecalactone gamma Coeur | 0.20 |
| Dihydro beta ionone BHT | 0.20 |
| Total: | 95.00 |

4-(3,3-Dimethyl-bicyclo[2.2.1]hept-2-yl)-1-methyl-2-oxa-bicyclo[2.2.2]octane imparted woody, animalic, phenolic in water, leather, amber, sweet, and slightly fruity characters to a fragrance formula.

What is claimed is:

1. A compound:

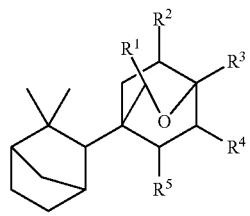

wherein $R^1$, $R^2$, $R^3$, $R^4$, and $R^5$ are independently selected from the group consisting of hydrogen and $C_1$-$C_5$ alkyl.

2. The compound of claim 1, wherein the compound is 4-(3,3-dimethyl-bicyclo[2.2.1]hept-2-yl)-2-oxa-bicyclo[2.2.2]octane.

3. The compound of claim 1, wherein the compound is 4-(3,3-dimethyl-bicyclo[2.2.1]hept-2-yl)-1-methyl-2-oxa-bicyclo[2.2.2]octane.

4. The compound of claim 1, wherein the compound is 4-(3,3-dimethyl-bicyclo[2.2.1]hept-2-yl)-5-methyl-2-oxa-bicyclo[2.2.2]octane.

5. The compound of claim 1, wherein the compound is 4-(3,3-dimethyl-bicyclo[2.2.1]hept-2-yl)-1,5-dimethyl-2-oxa-bicyclo[2.2.2]octane.

6. A fragrance formulation containing an olfactory acceptable amount of a compound:

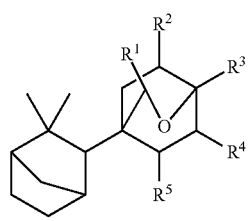

wherein $R^1$, $R^2$, $R^3$, $R^4$, and $R^5$ are independently selected from the group consisting of hydrogen and $C_1$-$C_5$ alkyl.

7. The fragrance formulation of claim 6, wherein in the compound is 4-(3,3-dimethyl-bicyclo[2.2.1]hept-2-yl)-2-oxa-bicyclo[2.2.2]octane.

8. The fragrance formulation of claim 6, wherein the compound is 4-(3,3-dimethyl-bicyclo [2.2.1]hept-2-yl)-1-methyl-2-oxa-bicyclo[2.2.2]octane.

9. The fragrance formulation of claim 6, wherein the compound is 4-(3,3-dimethyl-bicyclo[2.2.1]hept-2-yl)-5-methyl-2-oxa-bicyclo[2.2.2]octane.

10. The fragrance formulation of claim 6, wherein the compound is 4-(3,3-dimethyl-bicyclo[2.2.1]hept-2-yl)-1,5-dimethyl-2-oxa-bicyclo[2.2.2]octane.

11. The fragrance formulation of claim 6 incorporated into a product selected from the group consisting of a perfume, a cologne, toilet water, a cosmetic product, a personal care product, a fabric care product, a cleaning product, and an air freshener.

12. The fragrance formulation of claim 11, wherein the cleaning product is selected from the group consisting of a detergent, a dishwashing composition, a scrubbing compound, and a window cleaner.

13. The fragrance formulation of claim 6, wherein the olfactory acceptable amount is from about 0.005 to about 50 weight percent of the fragrance formulation.

14. The fragrance formulation of claim 6, wherein the olfactory acceptable amount is from about 0.5 to about 25 weight percent of the fragrance formulation.

15. The fragrance formulation of claim 6, wherein the olfactory acceptable amount is from about 1 to about 10 weight percent of the fragrance formulation.

16. A method of improving, enhancing or modifying a fragrance formulation through the addition of an olfactory acceptable amount of a compound of formula:

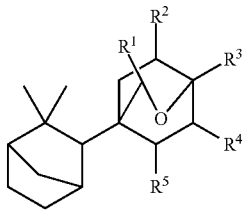

wherein $R^1$, $R^2$, $R^3$, $R^4$, and $R^5$ are independently selected from the group consisting of hydrogen and $C_1$-$C_5$ alkyl.

17. The method of claim 16, wherein the compound is selected from the group consisting of
  4-(3,3-dimethyl-bicyclo[2.2.1]hept-2-yl)-2-oxa-bicyclo[2.2.2]octane;
  4-(3,3-dimethyl-bicyclo[2.2.1]hept-2-yl)-1-methyl-2-oxa-bicyclo[2.2.2]octane;
  4-(3,3-dimethyl-bicyclo[2.2.1]hept-2-yl)-5-methyl-2-oxa-bicyclo[2.2.2]octane;
  4-(3,3-dimethyl-bicyclo[2.2.1]hept-2-yl)-1,5-dimethyl-2-oxa-bicyclo[2.2.2]octane; and
  a mixture thereof.

18. The method of claim 16, wherein the olfactory acceptable amount is from about 0.005 to about 50 weight percent of the fragrance formulation.

19. The method of claim 16, wherein the olfactory acceptable amount is from about 0.5 to about 25 weight percent of the fragrance formulation.

20. The method of claim 16, wherein the olfactory acceptable amount is from about 1 to about 10 weight percent of the fragrance formulation.

* * * * *